United States Patent [19]

Frackelton, Jr. et al.

[11] Patent Number: 4,543,439

[45] Date of Patent: Sep. 24, 1985

[54] PRODUCTION AND USE OF MONOCLONAL ANTIBODIES TO PHOSPHOTYROSINE-CONTAINING PROTEINS

[75] Inventors: A. Raymond Frackelton, Jr., East Providence, R.I.; Herman N. Eisen, Waban, Mass.; Alonzo H. Ross, Bensalem, Pa.

[73] Assignee: Massachusetts Institute of Technology, Cambridge, Mass.

[21] Appl. No.: 449,355

[22] Filed: Dec. 13, 1982

[51] Int. Cl.[4] .................... C12N 15/00; G01N 33/54; G01N 33/56; G01N 33/60

[52] U.S. Cl. .................................... 935/92; 435/240; 435/948; 435/4; 435/7; 435/15; 435/68; 935/104; 935/108; 935/110; 436/514; 436/518; 436/536; 436/537; 436/539; 436/540; 436/541; 436/542; 436/548; 436/804; 436/813; 436/815; 436/821; 436/823; 260/112 R

[58] Field of Search ................... 424/DIG. 1, 85, 177; 435/7, 15, 68, 70, 172.2, 240, 948; 436/514–516, 518, 528, 529–531, 536–542, 548, 804, 813, 815, 821, 823; 260/112 R, 112.5 R; 935/95, 92, 99, 100, 102, 103, 104, 106, 108, 110

[56] References Cited

PUBLICATIONS

Ross, A. H. et al., Nature, vol. 294, pp. 654–656 (1981).
Veronese, F. et al., J. Virology, vol. 4313, pp. 896–904 (9–1982).
Hunter, Tony & Sefton, B. M. "Transforming Gene Product of Rous Sarcoma Virus Phosphorylates Tyrosine", Proc. Natl. Acad. Sci., U.S.A., vol. 77, No. 3, pp. 1311–1315, Mar. 1980.
Oi, Vernon T. & Herzenberg, L. A., "Immunoglobulin-Producing Hybrid Cell Lines" Selected Methods in Cellular Immunology, Ed. Mishell & Shiigi, pp. 351–371, Pub. W. H. Freeman & Co., San Francisco, CA.
Ushiro, Hiroshi & Cohen, S. "Identification of Phosphotyrosine as a Product of Epidermal Growth Factor-Activated Protein Kinase in A-431 Cell Membranes: The Journal of Biological Chemistry, vol. 255, No. 18, Sep. 25, 1980, pp. 8363–8365.
Witte, Owen N., Dasqupta, A. & Baltimore, D., Nature, vol. 283, Feb. 28, 1980, pp. 826–831.

*Primary Examiner*—Ben R. Padgett
*Assistant Examiner*—M. Moskowitz
*Attorney, Agent, or Firm*—Arthur A. Smith, Jr.; Thomas J. Engellenner

[57] ABSTRACT

A hybridoma cell line is disclosed that secretes monoclonal antibodies which serve as a high titer, reproducible, biological reagent useful in biological/medical research for isolating and identifying phosphotyrosine-containing proteins. In addition, the antibodies have potential uses in diagnosis of a variety of diseases, including certain cancers. The antibodies, which have demonstrated affinity for a variety of molecules containing o-phosphotyrosine residues, were prepared using a synthetic analog, p-azobenzyl phosphonate (ABP) covalently linked to a carrier protein, as the antigen.

32 Claims, No Drawings

PRODUCTION AND USE OF MONOCLONAL ANTIBODIES TO PHOSPHOTYROSINE-CONTAINING PROTEINS

BACKGROUND OF THE INVENTION

The U.S. Government has rights in this invention pursuant to National Institute of Health Grant No. NIH-S-RO1-CA15472-08.

Attention is directed to an article by two of the inventors and a colleague, entitled "Phosphotyrosine-Containing Proteins Isolated by Affinity Chromatography with Antibodies to a Synthetic Hapten", 294 Nature 654–656, (December 1981), herein incorporated by reference.

The cell line of this invention has been deposited with the American Type Culture Collection 12301 Parklawn Drive, Rockville, Md. 20852, on Dec. 3, 1982. The coding number is HB 8190.

Protein kinases that add phosphate to the hydroxyl group of tyrosine have been strongly implicated in the control of cellular growth. Oncogenic transformation of cells by many retroviruses, such as the Rous sarcoma virus, the Abelson murine leukemia virus, feline sarcoma virus, Fujinami sarcoma virus, and others, results in a 10–20 fold increase in phosphotyrosine on both the virally encoded transforming-proteins and on several cellular proteins. It has been shown in the Rous system (and is likely true in the other viral systems) that the virally encoded transforming-protein is a tyrosine kinase, and that its kinase activity is necessary both for autophosphorylation and for maintenance of the transformed state of the cell.

The viral oncogenes encoding tyrosine kinases also have cellular homologues from which the viral genes are believed to have been derived. That finding implies that tyrosine-kinases have some normal role in growth control, perhaps during embryonic development, regeneration or even normal growth. In fact, poly-A rich RNA that hybridizes with retroviral oncogenes has been found in untransformed, as well as transformed, cells. Furthermore, normal cells have been shown to express proteins homologous to the Abelson and Rous transforming proteins.

Direct evidence for the involvement of tyrosine kinases in the regulation of normal cell growth has come from studies of the interactions of polypeptide growth factors with their target cells. The binding of epidermal growth factor (EGF) to human epidermal carcinoma cells results in the very rapid phosphorylation of the EGF receptor (and other cellular proteins) on tyrosine residues. Similar tyrosine phosphorylations of receptors for platelet derived growth factor and insulin have recently been demonstrated in response to binding of platelet derived growth factor and insulin, respectively.

There exists a need for antibodies that bind phosphotyrosine-containing proteins (PT-proteins). In particular, monoclonal antibodies can facilitate the identification of cellular substrates for tyrosine kinases and make possible affinity purification of their substrates. Moreover, to the extent that PT-proteins and the like are implicated in tumor growth and normal cell growth, antibodies to such proteins may have clinical applications in screening for, and detecting, diseases.

SUMMARY OF THE INVENTION

We have constructed and isolated a hybridoma cell line that secretes monoclonal antibodies to PT-proteins. These monoclonal antibodies serve as a high titer, reproducible, biological reagent useful in biological/medical research for isolating and identifying phosphotyrosine-containing proteins. In addition, the antibodies have potential uses in diagnosis of a variety of diseases, including certain cancers. The antibodies, which have demonstrated affinity for a variety of molecules containing O-phosphotyrosine residues, were prepared using a synthetic analog, p-azobenzyl phosphonate (ABP) covalently linked to a carrier protein, as the antigen.

In particular, affinity for PT-proteins has been shown with transforming proteins from cells infected with Abelson murine leukemia virus, and with the EGF receptor protein, and with a variety of cellular PT-proteins. The specificity of the antibodies of our cell line for PT-proteins has been demonstrated by their comparative inactivity with phosphoamino acids other than phosphotyrosine. Virtually no affinity was shown for phosphoserine and phosphotheronine-analogs; those amino acids generally account for 99.9 percent of the phosphorylated protein in typical cells.

In another aspect of our invention, various assay methods are disclosed for detecting PT-proteins using the antibodies of our cell line. Tumor growth factors (TGF) believed to be associated with various cancers can be detected by their phosphorylation of tyrosine residues on cellular receptors, such as epidermal growth factor (EGF) receptors. Similar reactions can be found for platelet-derived growth factor. Assay methods are disclosed for detecting such growth factors that could be use clinically.

Our antibodies are classified as $\gamma_1 K$ immunoglobulins and have a molecular weight of about 150,000. They are further characterized as also having a weak affinity to 5' mononucleotides. The binding clearly has an ionic component and it is believed that our antibodies are strongly attracted to doubly ionized phosphate groups at physiological conditions; at pH below 6 less affinity is seen, presumably due to lack of doubly ionized phosphate groups. Our antibodies are sensitive to ionic detergents and to high ionic strength. The sensitivity to high ionic strength provides an advantage in their use, in that PT-proteins can be dissociated from the immunosorbent beads using the gentle, non-denaturing conditions of high salt. And furthermore, the immunosorbent beads (or other matrices) can be gently regenerated and used again and again.

DETAILED DESCRIPTION OF THE PREFERRED EMBODIMENTS

A hybridoma secreting monoclonal antibodies that bind to PT-residues of PT-proteins was isolated from a fusion of Sp 2/0 cells with spleen cells of mice immunized with the ABP analog of the target antigenic determinant. Male 8-weeks old Balb/c mice were immunized intradermally and in their footpads with 100 µg of Keyhole Limpet Hemocyanin (KLH) carrier derivatized with about 30 ABP groups per 100,000 MW of KLH and emulsified in complete Freunds adjuvant. The mice were injected again about 3 months later with the same antigen. Four days later, spleens were removed from four mice killed by ether and cell suspensions prepared.

The spleen cells ($1.6 \times 10^8$) from immunized mice and the Sp 2/0 fusing partner cells ($8 \times 10^7$) were each washed three times with serum free Dulbecco's Modified Eagles (DME) media, then mixed together and centrifuged at 400×g for 5 minutes at room temperature. The cell pellet was resuspended in 0.2 ml DME and re-centrifuged at 400×g for 10 minutes. The spleen and Sp 2/0 cells were fused using polyethylene glycol (MW=1500, Behringwerke). Fused cells were grown in HAT medium.

Hybrids that secrete anti-ABP antibody were detected by a solid phase radioimmunoassay. Wells of plates (Dynatech) were coated overnight with ABP-BSA (50 μl of 2 μg ml$^{-1}$ solution in PBS), then washed with PBS and a 1% BSA solution in PBS. Twenty-five microliters of 1% of BSA and 20 μl of culture fluid were pipetted into each well and incubated for 3 hours at 37° C. The wells were next washed 2-times with PBS, and 50 μl of a solution containing $^{125}$I-labeled rabbit anti-mouse Ig (20 μg ml$^{-1}$, 2.5×10$^4$ cpm ng$^{-1}$) (Gateway, affinity purified on a normal mouse Ig-Sepharose 4B immunosorbent and labeled by the chloramine T method) were added to each well and incubated 4 hours at 37° C. The wells were washed three times with PBS, and remaining $^{125}$I was determined in a scintillation spectrometer. Specificity of antibody was shown by the ability of ABP-BSA to inhibit antibody binding to ABP-BSA coated wells.

Hybrids producing anti-ABP antibody were cloned by the limiting dilution method. Cloned hybridoma cells producing anti-ABP antibody were grown as an ascites in Balb/c mice primed with 0.5 ml pristane one day earlier. Monoclonal antibody was purified from ascites fluid by precipitation at 50% saturated ammonium sulfate followed by affinity chromatography on phosphotyramine-derivatized Sepharose 4B. (The derivatized-Sepharose 4B was prepared by phosphorylating tyramine with P$_2$O$_5$ and coupling the product to cyanogen bromide (CNBr)-activated Sepharose 4B).

A rigorous and important test of the specificity of our monoclonal antibody was to determine if the antibody bound other phosphoamino acids. Accordingly, our antibody was coupled to CNBr activated Sepharose 4B at both 5 mg per ml and 15 mg per ml of Sepharose; immunosorbent was packed into 1 ml syringe-columns. Pure ($^{32}$P)-phosphotyrosine (PTYR) and ($^{32}$P)-phosphoserine (PSER) were prepared from a crude preparation of Abelson cells kinased in vitro with ($^{32}$P)-γ-ATP. The kinase mixture was precipitated with TCA and partially hydrolyzed with 6N HCl. Phosphoamino acids were resolved from the hydrolysate by high voltage paper electrophoresis at pH 3.5, and radioactivity co-migrating with unlabeled phosphoamino acid standards was eluted with water. Purity of the ($^{32}$P)-phosphoamino acids was confirmed by cellulose thin layer chromatography in a solvent system consisting of a mixture of saturated ammonium sulfate, sodium acetate, and isopropanol. The ability of antibody-Sepharose to bind ($^{32}$P)-phosphotyrosine is shown in Table I. The PTYR bound quantitatively to our antibody coupled at 5 mg/ml of Sepharose, and could not be washed off the immunosorbent with 10 column volumes of RIPAND buffer (additionally containing 0.1% sodium dodecyl sulfate and 0.5% sodium deoxycholate). That PTYR was specifically bound to the antibody was shown by the complete recovery of PTYR upon elution with phenyl phosphate hapten. In contrast, PSER failed to bind to the Sepharose, even when the immunosorbent bore 15 mg/ml of antibody.

TABLE I

Proportion of $^{32}$P—phosphoamino acids that immunospecifically bind to monoclonal antibody 2G8-Sepharose

| Fraction from Antibody-Sepharose Column | Amount of Antibody Coupled per ML of Sepharose | | | |
|---|---|---|---|---|
| | 5 mg | | 15 mg | |
| | PTYR | PSER | PTYR | PSER |
| flowthru | 0.01 | 0.93 | 0.02 | 0.93 |
| wash | 0 | 0.01 | 0 | 0.01 |
| hapten eluate | 0.99 | 0 | 1.00 | 0 |

In other tests our antibody was used to purify small batches of phosphotyrosine-proteins. In order to remove molecules that bind non-specifically to protein-Sepharose, detergent extracts of $^{32}$P-labeled cells were mixed with 100 μl of BSA covalently coupled to Sepharose 4B at 10 mg ml$^{-1}$ of Sepharose, and the mixture was incubated on a shaker at 4° C. for 1 hour. The "pre-adsorbed" extract was collected by centrifugation through a pinhole and next adsorbed with 50 μl of our antibody that had been coupled to CNBr activated Sepharose. After a 1 hour incubation at 4° C., the mixture was centrifuged and the supernatant removed. The anti-phosphotyrosine-Sepharose beads were washed three times with 1 ml of a RIPAND buffer and once with 1 ml of RIPAND buffer lacking BSA. RIPAND buffer contained 1% Triton X-100, 5 mM Na$_2$EDTA, 150 mM NaCl, 100 Kallikrein units aprotinin ml$^{-1}$, 1 mg ml$^{-1}$ BSA, 1 mM phenylmethylsulfonyl fluoride, 10 mM TRIS buffer, pH 7.4.

Phosphotyrosine-proteins were immunospecifically eluted from the immunosorbent with 40 μl of a solution containing 40 mM phenyl phosphate, 1% Triton X-100, 50 mm NaCl, 3.3 mM Tris(tris-hydroxymethylaminomethane), 1 mM PMSF, 100 kallikrein units aprotinin ml$^{-1}$ and 0.1 mg ml$^{-1}$ ovalbumin. After 10 minutes at 0° C., the eluate was collected by centrifugation through a pinhole. Portions of eluates were subjected to analysis by SDS polyacrylamide gel electrophoresis. The gels were fixed, dried on paper and $^{32}$P-bands visualized by autoradiography. Other portions of eluates were analyzed for phosphoamino acids by partial acid hydrolysis and subsequent thin layer electrophoresis.

To show usefulness in purifying cellular PT-proteins, our antibodies were employed with extracts of ANN-1 cells, a fibroblast cell line that had been transformed by Abelson leukemia virus. The ANN-1 cells were incubated in vivo with ($^{32}$P)-orthophosphate and then extracted with RIPAND buffer. The extracts were adsorbed to the antibody-Sepharose substrate using the batch procedure described above, washed in RIPAND and eluted with hapten. The eluate was analyzed by SDS polyacrylamide gel electrophoresis and displayed prominent bands of 116,000; 92,000; 76,000; 62,000; 39,000; and 30,000 daltons.

We next tested the performance of the antibodysorbent in another system known to contain phosphotyrosine proteins. Stimulation with epidermal growth factor (EGF) of human epidermal cells (A431) is known to result in tyrosine phosphorylation of the EGF receptor and of at least two other polypeptides. Therefore, A431 cells were labeled with ($^{32}$P)-orthophosphate for 3 hours, then stimulated with EGF at 75 ng/ml for 30 minutes at 37° C. RIPAND cell extracts were processed as described above and immunoadsorbed to the antibody Sepharose beads. Phosphoaminoacid analysis of the hapten eluate showed that 40% of the ($^{32}$P)-phosphoamino acids were phosphotyrosine; the eluate also had 4.5-times more PTYR than the eluate had from parallel A431 cultures not stimulated with EGF. SDS gel electrophoresis of the hapten eluates revealed a very dominant EGF-stimulated band of MW$_r$ 170,000 (the EGF receptor), as well as EGF-stimulated bands of variable intensity at 80,000, 60,000, 52,000, and 32,000 daltons.

Comparison of PTYR-proteins of various Abelson transformed cells may reveal common tyrosine kinase substrates that are intimately involved in maintainence of the transformed state. In addition, substrates may be found that are specific for certain transformed cell types, and that, therefore, may serve as new markers of cellular differentiation. Accordingly, 2M3, an Abelson transformed pre-B-lymphocyte was incubated with (32P)-orthophosphate, extracted with RIPAND and examined for PTYR-proteins, as described above. Hapten eluate of immunoadsorbed 2M3 contained in the ($^{32}$P)-phosphoamino acids, 45% PTYR, 50% PSER and about 5% PTHR; SDS polyacrylamide gel analysis revealed prominent bands shared with ANN-1 at 116,000, 62,000 and 39,000 daltons. Phosphoproteins apparently unique to 2M3 are observed at 53,000, 34,000, 32,000 and 30,000 daltons while those found only in ANN-1 were observed at 92,000, 76,000, 58,000, 43,500, and 36,000 daltons. 2M3 gel bands at MW$_r$ 116,000, 62,000, 53,000 and 39,000 contained an estimated 30%, 55%, 60%, and 80% phosphotyrosine, respectively.

CLINICAL APPLICATIONS

Our cell line and methods can be employed to identify other cellular substrates for tyrosine kinases and make possible the affinity purification of a wide variety of PT-proteins. Specifically, our antibodies may be employed in assays for tumor growth factors (TGF), associated with particular cancers or platelet-derived growth factor (PDGF) and its cellular receptor, involved in the development of arteriosclerosis.

In a simple TGF assay method, a biological fluid, such as urine or blood serum, or other potential source of TGF from a patient can be reacted with a preparation of EGF receptors, for example, cell membranes from A431, a human epidermal carcinoma cell line with numerous EGF receptors per cell. Adenosine triphosphate (labeled in the γ-phosphate with radioactive $^{32}$P or a thio analog labeled with $^{35}$S) is added as a source of phosphate. In the presence of TGF, the EGF receptor will incorporate labeled phosphate into its tyrosine residues. The reaction may then be terminated and the receptors extracted from the membrane. The receptors are then bound to monoclonal antibodies from our cell line (for example, this can be done using beads or the like coated with antibodies) and the radioactivity counted to provide a measure of the growth factor present in the sample. Assays for PDGF would follow a similar procedure employing a PDGF-sensitive receptor. Other assays may employ nerve growth factor receptors, insulin receptors, insulin-like growth factor receptors, sarcoma growth factor receptors and the like. Various modifcations to these methods as well as other assay teachniques employing our antibodies may be devised by those skilled in the art without departing from the spirit or scope of invention.

We claim:

1. A monoclonal antibody of the class IgG or IgM, derived from the fusion of a murine myeloma cell and a murine antibody-producing lymphoid cell, demonstrating specific reactivity to a phosphotyrosine moiety on phosphotyrosine-containing proteins.

2. The monoclonal antibody of claim 1 wherein the antibody demonstrates positive detection of antigenic determinants of phosphotyrosine-containing proteins by immunosorbent and electrophoretic assays.

3. The antibody of claim 1 wherein the antibody is further classified as a $\gamma_1$K antibody and has a molecular weight of about 150,000 daltons.

4. The monoclonal antibody of claim 1 wherein the antibody demonstrates:
   (a) positive reaction with phosphotyrosine containing proteins; and
   (b) lack of reactivity with phosphoserine or phosphorthreonine proteins.

5. The antibody of claim 1 wherein the antibody demonstrates positive reactivity with phosphotyrosine-containing proteins from animal cells.

6. The antibody of claim 1 wherein the antibody demonstrates positive reactivity with phosphotyrosine-containing proteins from human cells.

7. A murine hybridoma cell line characterized by its production of monoclonal antibodies of the class IgG or IgM demonstrating specific reactivity to a a phosphotyrosine moiety on phosphotyrosine-containing proteins.

8. The cell line of claim 7 wherein the antibodies demonstrate positive detection of antigenic determinants of phosphotyrosine containing proteins by immunosorbent and electrophoretic assays.

9. The cell line of claim 7 wherein the antibodies each have a molecular weight of about 150,000 daltons and are classified as $\gamma_1$K antibodies.

10. The cell line of claim 7 wherein the antibodies demonstrate:
    (a) positive reaction with phosphotyrosine-containing proteins; and
    (b) lack of reactivity with phosphoserine or phosphothreonine-containing proteins.

11. The cell line of claim 7 wherein the antibodies demonstrate positive reactivity with phosphotyrosine-containing proteins from animal cells.

12. The cell line of claim 7 wherein the antibodies demonstrate positive reactivity with phosphotyrosine-containing proteins from human cells.

13. An antibody-producing cell line having the identifying characteristics of ATCC HB 8190.

14. An immunosorbent material comprising the monoclonal antibodies of claim 1 and a microporous polymeric substrate.

15. The immunosorbent material of claim 14 wherein the substrate is a plurality of beads, each on the order of about 100 microns, in diameter.

16. The immunosorbent material of claim 14 wherein the substrate is polymerized agarose.

17. A process for producing antibodies of the class IgG or IgM to phosphotyrosine-containing proteins comprising: immunizing a murine animal with an antigen chosen from the group of phosphotyrosine, phosphotyrosine analogs and phosphotyrosine-containing proteins, forming fused cell hybrids between antibody-producing cells from the animal and murine myeloma cells, cloning the hybrids, and selecting the clones which demonstrate a specificity to antigenic determinants of a phosphotyrosine moiety on the phosphotyrosine-containing proteins.

18. The process of claim 17 wherein the step of immunizing the animal further comprises immunizing the animal with a synthetic hapten, azobenzylphosphonate.

19. A method of detecting the presence of phosphotryosine-containing proteins in a sample comprising the steps of contacting the sample with murine, hybridoma-derived, monoclonal antibodies of the class IgG or IgM, which antibodies demonstrate specificity for a phosphotyrosine moiety on phosphotyrosine-containing proteins; and testing for reactivity.

20. The method of claim 19 wherein the step of testing the sample further comprises contacting the sample with an immunosorbent material which includes the monoclonal antibodies.

21. The method of claim 19 wherein the step of testing further comprises testing by immunofluorescence.

22. The method of claim 19 wherein the step of testing further comprises testing by radioimmunoassay.

23. The method of claim 19 wherein the step of testing further comprises testing by immunoprecipitation.

24. The method of claim 19 wherein the step of testing further comprises testing by complement fixation.

25. The method of claim 19 wherein the step of testing further comprises testing by competitive reaction.

26. An assay method for measuring a sample to determine the concentration of growth factors which cause phosphorylation of tyrosine, the method comprising the steps of:
  (a) contacting the sample with a preparation of growth factor receptors;
  (b) adding a labeled source of phosphate;
  (c) extracting the receptors and contacting the extracted receptors with murine hybridoma-derived monoclonal antibodies of the class IgG or IgM which demonstrate specificity for a phosphotyrosine moiety on phosphotyrosine-containing proteins; and
  (d) measuring the amount of label bound to the antibodies to provide an indication of the amount of growth factor present in the sample.

27. The assay method of claim 26 wherein the step of contacting the sample with a preparation of growth factor receptors further comprises contacting the sample with growth factor receptors derived from an animal cell line.

28. The assay method of claim 26 wherein the step of contacting the sample with a preparation of growth factor receptors further comprises contacting the sample with growth factor receptors derived from a human cell line.

29. The assay method of claim 26 wherein the step of contacting the sample with a preparation of growth factor receptors further comprises contacting the sample with a preparation of epidermal growth factor receptors.

30. The assay method of claim 26 wherein the step of contacting the sample with a preparation of growth factor receptors further comprises contacting the sample with a preparation of platelet growth factor receptors.

31. The assay method of claim 26 wherein the preparation of growth factor receptors is a preparation of at least one type of receptor chosen from the group of epidermal growth factor receptors, platelet-derived growth factor receptors, nerve growth factor receptors, insulin receptors, insulin-like growth factor receptors, and sarcoma growth factor receptors.

32. The assay method of claim 26 wherein the step of adding a labeled source of phosphate further comprises adding radioactive adenosine triphosphate.

* * * * *